United States Patent
Maschke et al.

(10) Patent No.: US 8,606,348 B2
(45) Date of Patent: Dec. 10, 2013

(54) SYSTEM AND METHOD FOR PERFORMING AT LEAST ONE OF A VERTEBROPLASTY PROCEDURE, A KYPHOPLASTY PROCEDURE, AN ELECTROENCEPHALOGRAPHY (EEG) PROCEDURE AND INTRAOPERATIVE ELECTROMYOGRAPHY (EMG) PROCEDURE USING A ROBOT-CONTROLLED IMAGING SYSTEM

(75) Inventors: Michael Maschke, Lonnerstadt (DE); Oliver Meissner, Munich (DE)

(73) Assignee: Siemens Aktiengesellschaft, Munich (DE)

(*) Notice: Subject to any disclaimer, the term of this patent is extended or adjusted under 35 U.S.C. 154(b) by 843 days.

(21) Appl. No.: 11/878,085

(22) Filed: Jul. 20, 2007

(65) Prior Publication Data

US 2009/0024025 A1    Jan. 22, 2009

(51) Int. Cl.
*G03B 42/02*    (2006.01)

(52) U.S. Cl.
USPC ............................... 600/427; 600/425

(58) Field of Classification Search
USPC ............... 600/425; 378/197; 5/600–624
See application file for complete search history.

(56) References Cited

U.S. PATENT DOCUMENTS

| | | | |
|---|---|---|---|
| 4,894,855 A | 1/1990 | Kresse | |
| 6,351,678 B1* | 2/2002 | Borders | 700/83 |
| 6,435,715 B1* | 8/2002 | Betz et al. | 378/197 |
| 6,869,217 B2* | 3/2005 | Rasche et al. | 378/197 |
| 6,990,368 B2 | 1/2006 | Simon et al. | |
| 7,112,205 B2 | 9/2006 | Carrison | |
| 7,596,254 B2* | 9/2009 | Liebschner et al. | 382/128 |
| 2004/0210231 A1* | 10/2004 | Boucher et al. | 606/93 |
| 2005/0228255 A1* | 10/2005 | Saracen et al. | 600/407 |
| 2005/0228397 A1 | 10/2005 | Malandain et al. | |
| 2006/0120507 A1 | 6/2006 | Brunner et al. | |

FOREIGN PATENT DOCUMENTS

| | | |
|---|---|---|
| DE | 10 2005 012 700 | 9/2006 |
| EP | 0 220 501 | 5/1989 |

OTHER PUBLICATIONS

Lee et al., Closed reduction vertebroplasty for the treatment of osteoporotic vertebral compression fractures, Apr. 2004, Journal of Neurosurgery, vol. 100, Issue 4 Suppl Spine, p. 392-396.*

* cited by examiner

*Primary Examiner* — Jacqueline Cheng
(74) *Attorney, Agent, or Firm* — Harness, Dickey & Pierce, P.L.C.

(57) ABSTRACT

In one embodiment, the present application is directed to a method. The method includes performing at least one of, or a portion of one of, a vertebroplasty procedure, a kyphoplasty procedure, an electroencephalography (EEG) procedure and intraoperative electromyography (EMG) on a patient, and using an imaging system to image at least a portion of the patient during performance of at least a portion of this procedure), the imaging system being arranged on a robot including at least four, preferably six axes of rotation. In another embodiment of the present application, an x-ray system is disclosed. The x-ray system includes an imaging system including an x-ray source and an x-ray detector; a table; and at least two robots. The table is movable by the at least one robot and the at least one other robot includes at least four, preferably six axes of rotation and controls movement of the imaging system.

28 Claims, 12 Drawing Sheets

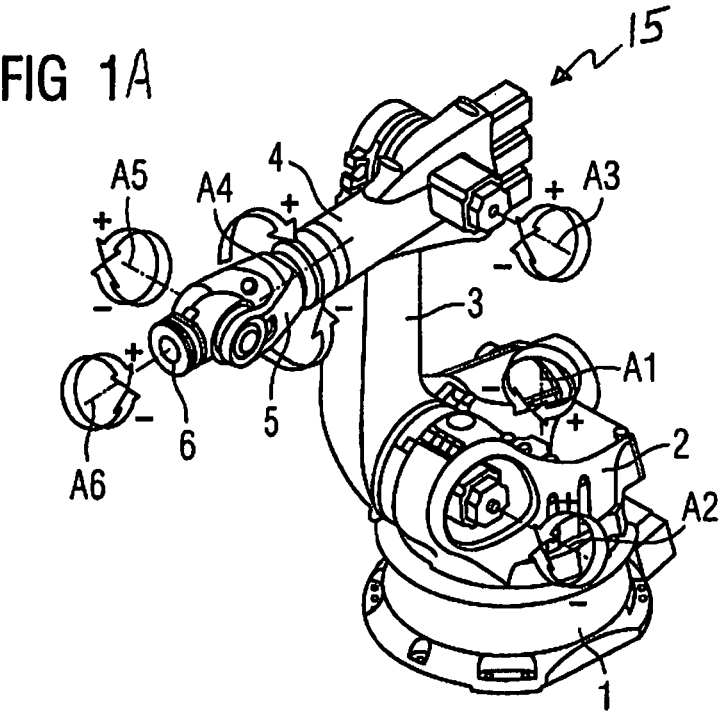
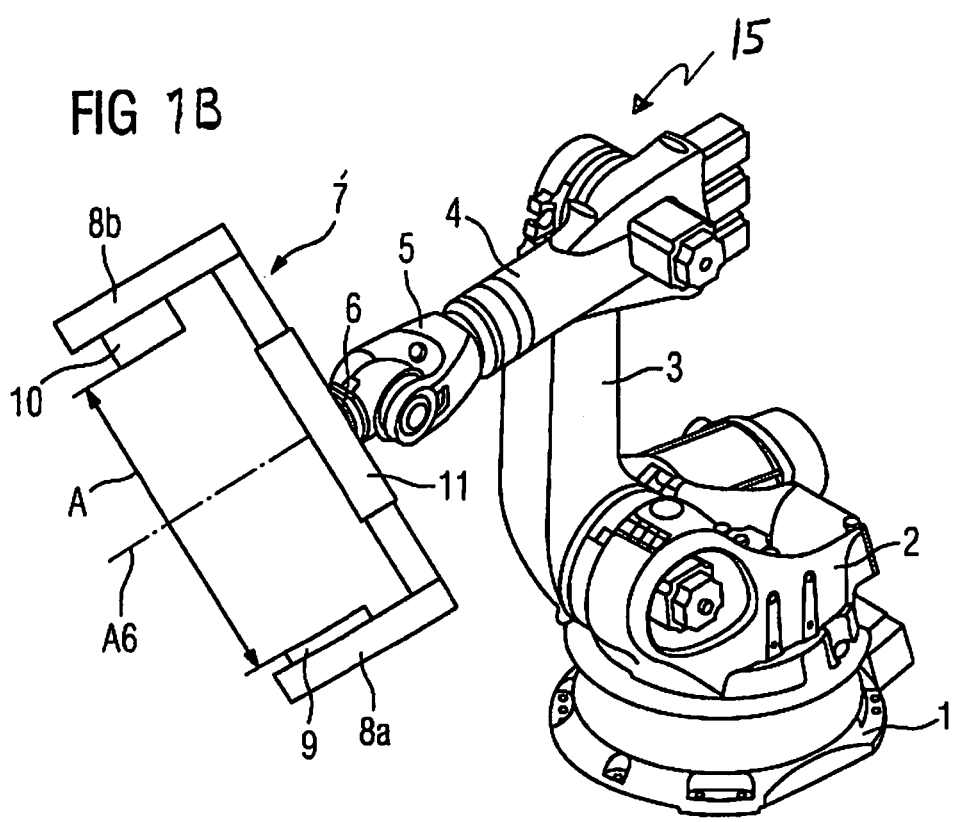

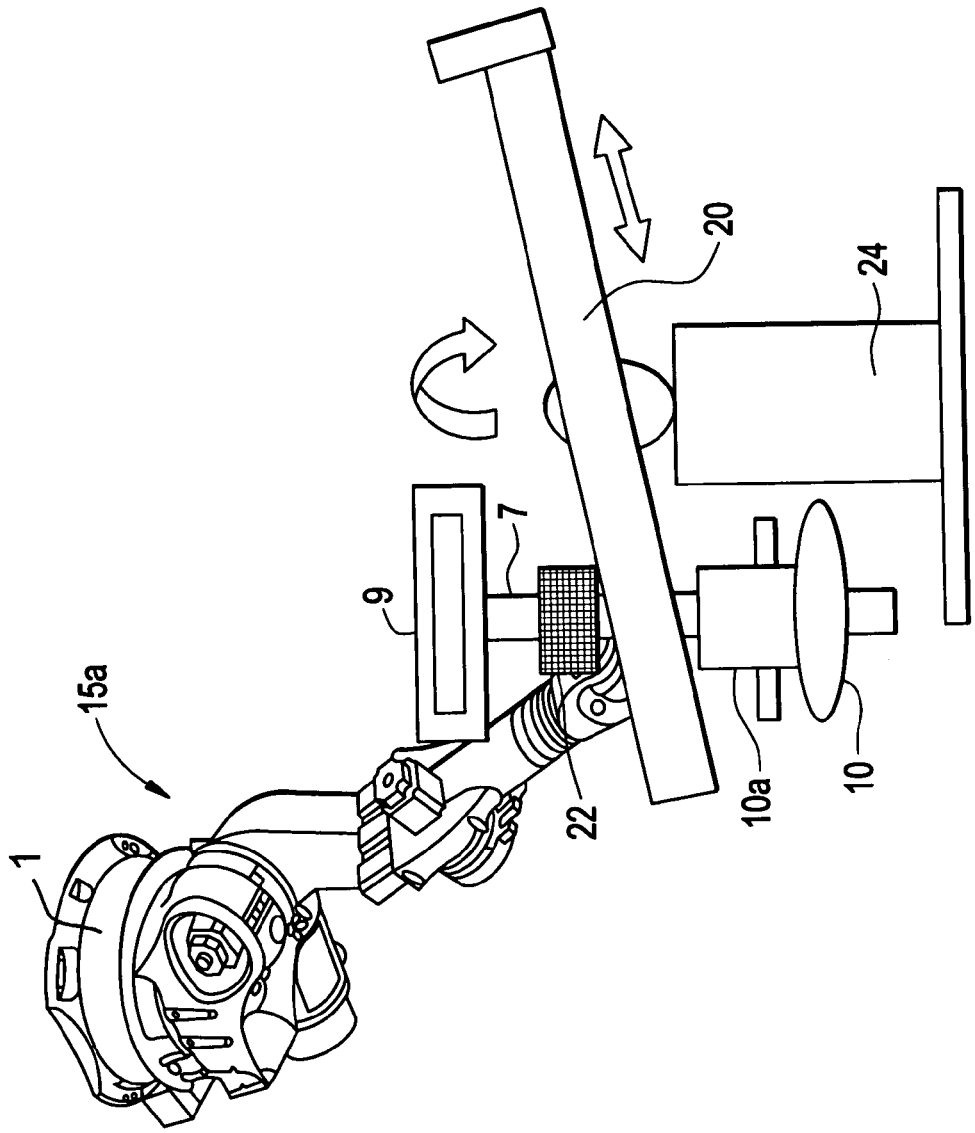

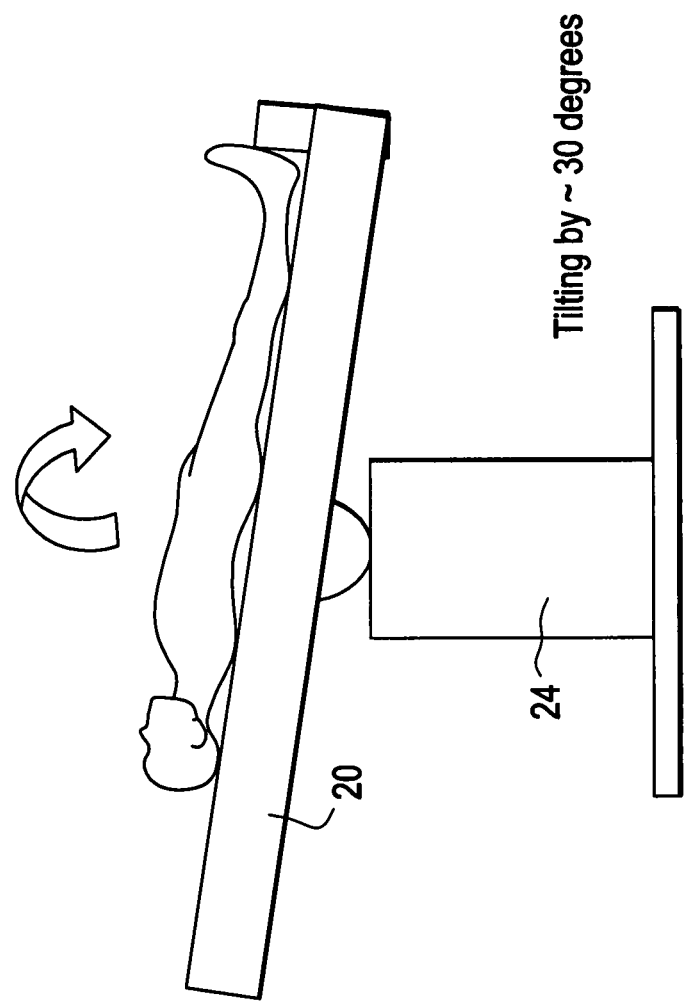

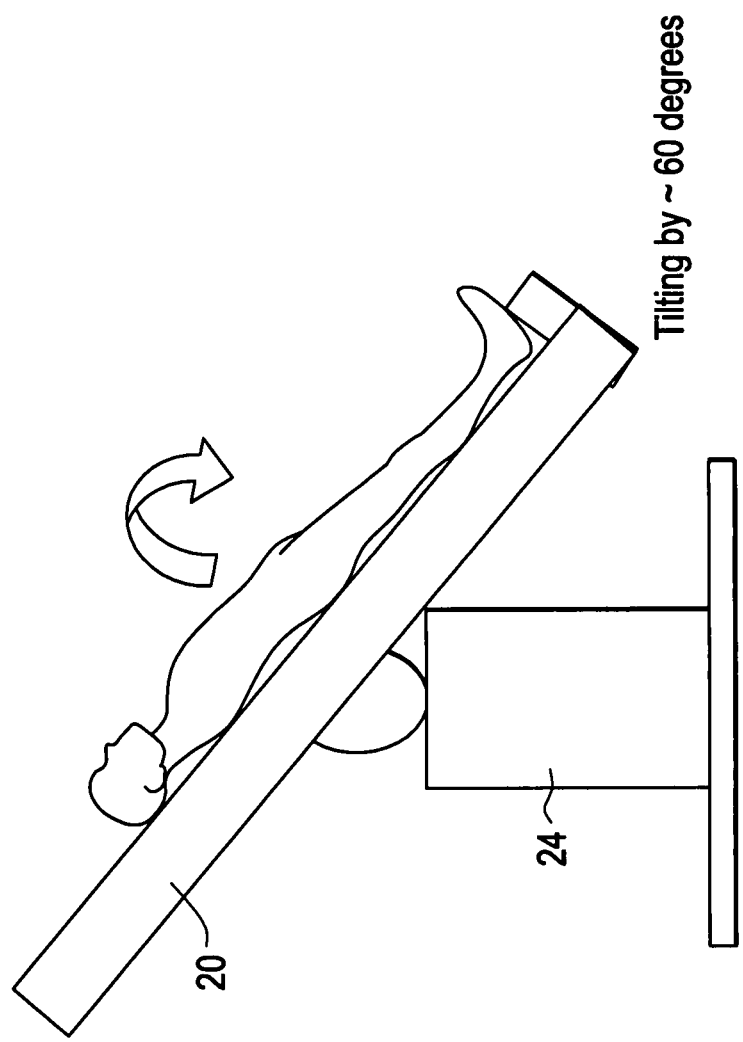

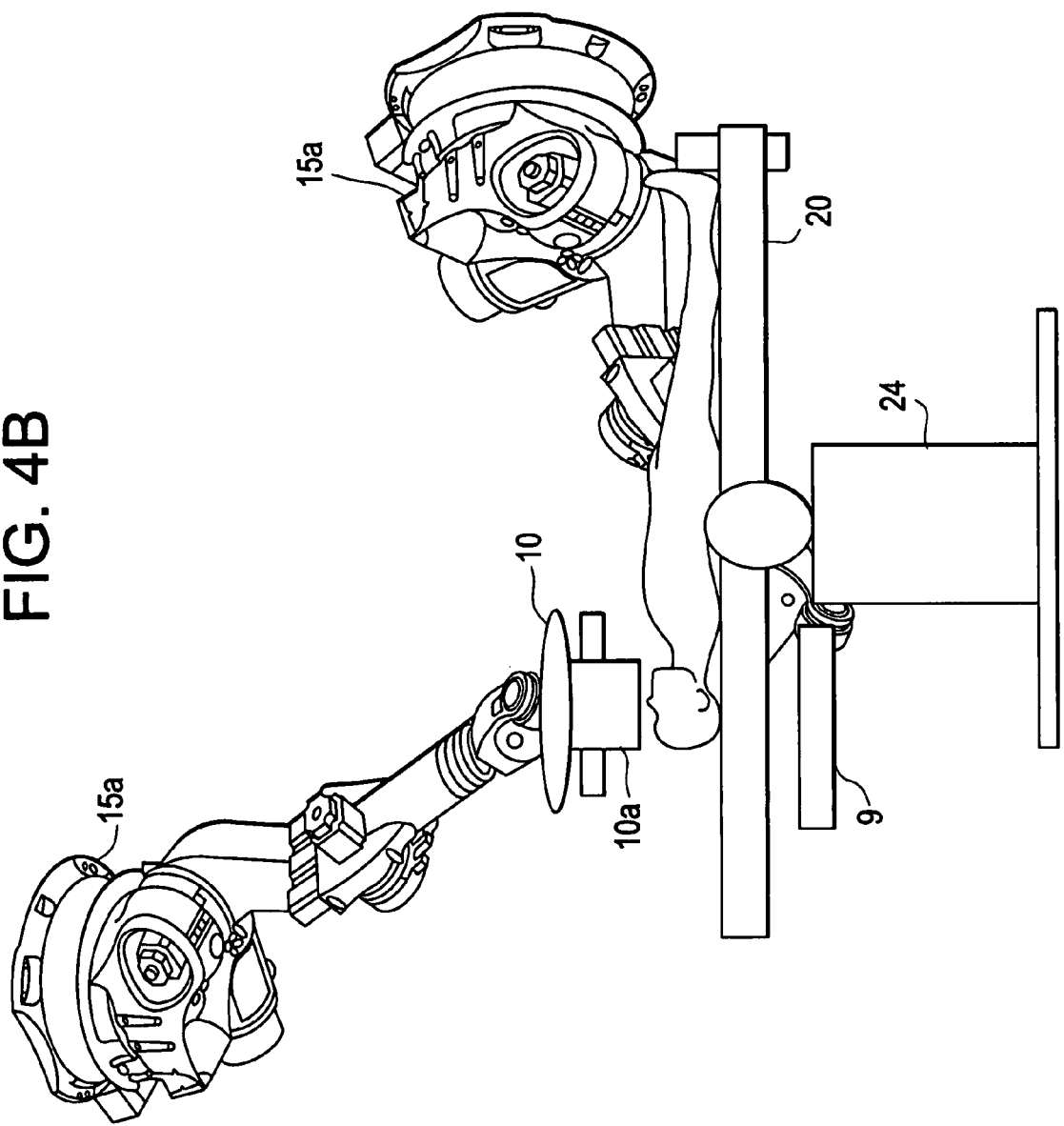

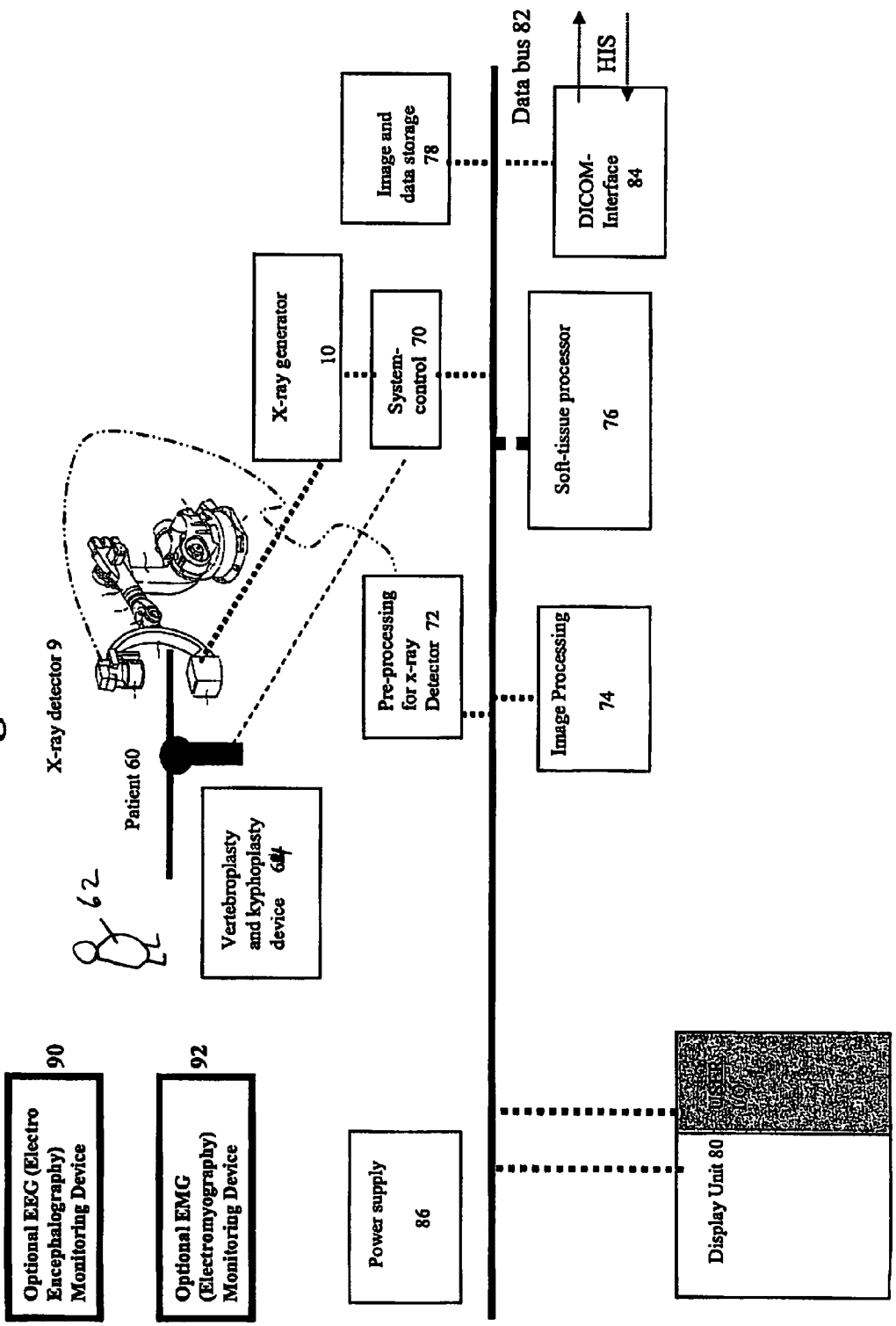

SYSTEM AND METHOD FOR PERFORMING AT LEAST ONE OF A VERTEBROPLASTY PROCEDURE, A KYPHOPLASTY PROCEDURE, AN ELECTROENCEPHALOGRAPHY (EEG) PROCEDURE AND INTRAOPERATIVE ELECTROMYOGRAPHY (EMG) PROCEDURE USING A ROBOT-CONTROLLED IMAGING SYSTEM

FIELD

Embodiments of the present invention generally relate to systems and methods for performing at least one of a vertebroplasty procedure, a kyphoplasty procedure, an electroencephalography (EEG) procedure and intraoperative electromyography (EMG).

BACKGROUND

Osteoporosis is loss of calcium from bone resulting in weakened bone structure. Osteoporosis increases the risk of fracture of vertebral bodies. According to the Osteoporosis Foundation, ten million people have osteoporosis, including 45% of women over 50 years of age.

An estimated 700,000 osteoporosis-related vertebral compression fractures occur annually, resulting in 150,000 hospitalizations. In this type of fracture, the top of the vertebral body collapses down with a greater relative collapse in the front, thus producing "wedged vertebrae," a "Dowager's hump," a shortening of height, etc. The resulting change in height and spinal alignment can lead to serious health problems, including chronic or severe pain, limited function and reduced mobility, loss of independence in daily activities, decreased lung capacity, difficulty in sleeping, etc. Further, studies show that a first osteoporotic fracture makes it five times more likely for further fractures to occur.

Vertebroplasty and kyphoplasty are both minimally invasive interventional procedures for treating osteoporotic fractures. Vertebroplasty is defined as a percutaneous procedure, in which a cement-like material (such as, for example, polymethyl-methacrylat, PMMA) is injected through a needle directly into a fractured bone. U.S. Pat. No. 7,122,205 entitled "Apparatus and Methods for Delivering Compound into Vertebrae for Vertebroplasty", the entire contents of which are hereby incorporated herein by reference, describes one example of a vertebroplasty solution which provides bone cement into a vertebrae.

U.S. Pat. No. 6,990,368 entitled "Method and Apparatus for Virtual Digital Subtraction Angiography", the entire contents of which are hereby incorporated herein by reference, includes an example of a mobile x-ray system used for imaging in conjunction with a vertebroplasty treatment. Such a system has several disadvantages. For example, the mobile unit is on wheels, which provides a less rigid structure for precise 3D image reconstruction; as the mobile unit is on wheels, it can carry only low power x-ray tubes; no soft-tissue imaging can be performed with such an angiographic system; and although it is mobile, it is difficult to move into any precise position around a patient.

Kyphoplasty includes one step in addition to the vertebroplasty procedure. Prior to injecting the cement-like material into the fractured bone, a special balloon is inserted and gently inflated inside the fractured vertebrae. The goal of this step is to restore height to the bone, thus reducing deformity of the spine. Published United States Application 2005/0228397 entitled "Cavity Filling Device," the entire contents of which are hereby incorporated herein by reference, discloses an example method and apparatus for performing a kyphoplasty treatment.

Both vertebroplasty and kyphoplasty procedures are used to stabilize a vertebral fracture and provide immediate pain relief. Both procedures can both effectively treat hemangiomas of the vertebral body and may be palliative in patients with malignant pathologic fractures. Over 195,000 fractures have been treated with balloon kyphoplasty as of Oct. 31, 2005, and approximately 7,400 physicians worldwide have been trained to do the procedure. Results from clinical studies show that both procedures are safe and effective with low complication rates.

However, fractures of the vertebrae have traditionally been more difficult to manage and treat than broken bones in the hip or wrist, etc. The traditional treatment for fractures of the spine caused by osteoporosis, for example, has included pain reduction (medication), bed rest and bracing. Surgery on the spine is extremely difficult and risky, and has typically not been used to treat vertebral fractures associated with osteoporosis, except as a last resort.

Over the past 5-10 years, vertebroplasty and kyphoplasty have been considered as clinically accepted minimally invasive procedures to treat osteoporotic or metastic vertebral fractures. However, until now, there has been no agreement which imaging modality is best to guide and control the interventional procedural steps of vertebroplasty and kyphoplasty. While most operators rely on fluoroscopic imaging, others prefer CT (Computed Tomography) imaging, especially with the use of CT-fluoroscopy (real-time CT imaging with 2-4 images per second and slice thicknesses of 1-10 mm).

Both procedural imaging techniques, however, have several limitations. For example, with fluoroscopy alone, paravetebral soft-tissue is not visible and the cement-like material has difficulties being seen. With CT guidance alone, the real-time imaging may not be sufficient to follow the injection of the cement-like material in either the vertebroplasty or the kyphoplasty procedures. Furthermore, there is limited access to the patient and substantial radiation to the doctor when utilizing the CT-fluoroscopy procedure.

SUMMARY

In at least one embodiment, the present application is directed to a method. The method includes performing at least one of a vertebroplasty procedure, a kyphoplasty procedure, an electroencephalography (EEG) procedure and intraoperative electromyography (EMG) on a patient, and using an imaging system including at least an x-ray source and detector to image at least a portion of the patient during performance of at least a portion of the at least one of a vertebroplasty procedure, a kyphoplasty procedure, an electroencephalography (EEG) procedure and intraoperative electromyography (EMG), the imaging system being arranged on a robot including at least four axes of rotation, and preferably at least 6 axes of rotation.

In at least one further embodiment of the present application, an x-ray system is disclosed. The x-ray system includes an imaging system including an x-ray source and an x-ray detector; a table; and at least one robot. The table is movable by the at least one robot and the at least one other robot includes at least four axes of rotation, and preferably at least 6 axes of rotation and controls movement of the imaging system.

In at least one embodiment, a method includes imaging, using an imaging system including at least an x-ray source and detector, at least a portion of a patient during at least a portion of at least one of a vertebroplasty procedure, a kyphoplasty procedure, an electroencephalography (EEG) procedure and intraoperative electromyography (EMG). The imaging system is arranged on a robot including at least four axes of rotation, and preferably at least 6 axes of rotation.

Further, in at least one other embodiment, an x-ray system includes an imaging system including an x-ray source and an x-ray detector, a table, and at least two robots. The x-ray source and an x-ray detector are movable by the at least one robot and the at least one other robot, each including at least six axes of rotation to control movement.

BRIEF DESCRIPTION OF THE DRAWINGS

The present methods and systems are explained below with the aid of example embodiments in conjunction with the drawings, without restricting the scope of protection prescribed by the patent claims. In the drawings:

FIG. 1A illustrates an example embodiment of a robotic system including at least six axes of rotation and FIG. 1B illustrates an example embodiment of a robotic system including an x-ray source and x-ray detector and including at least six axes of rotation.

FIGS. 2A-2D illustrate an example embodiment of a ceiling mounted robotic system in combination with a tiltable table;

FIGS. 4A-4C illustrate an example embodiment of an imaging system, a table, and a plurality of robots, one for controlling the table and another for controlling the imaging system;

FIG. 7 illustrates an example embodiment of a system overview of example robotic systems for use in conjunction with at least one of an electroencephalography (EEG) procedure and intraoperative electromyography (EMG).

DETAILED DESCRIPTION OF EXAMPLE EMBODIMENTS

Figure 2B:
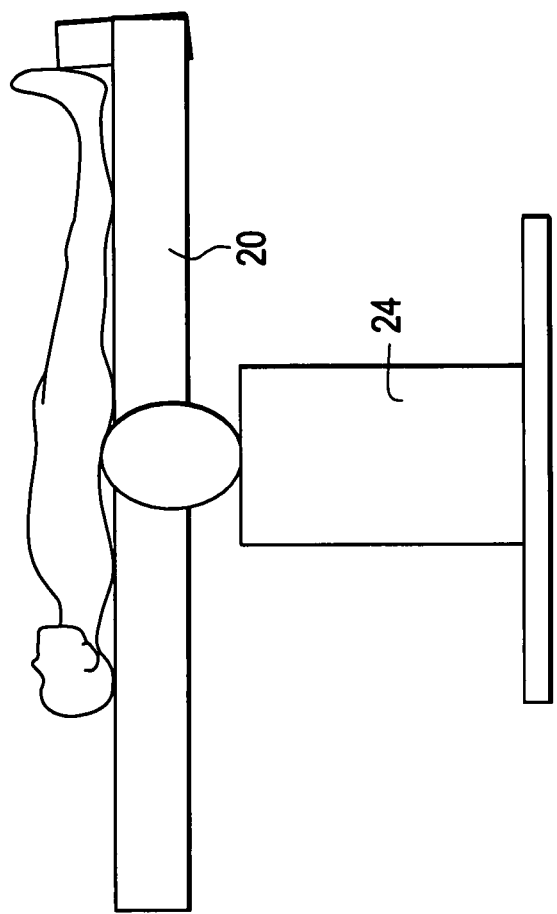

In at least one embodiment of the present application, a method is disclosed. The method includes imaging, using an imaging system including at least an x-ray source and detector, at least a portion of the patient during at least a portion of at least one of a vertebroplasty procedure, a kyphoplasty procedure, an electroencephalography (EEG) procedure and intraoperative electromyography (EMG). The imaging system is arranged on a robot including at least four axes of rotation, and preferably at least 6 axes of rotation. In at least one other embodiment, a method is disclosed which includes performing at least one of a vertebroplasty procedure, a kyphoplasty procedure, an electroencephalography (EEG) procedure and intraoperative electromyography (EMG) on a patient and using an imaging system, including at least an x-ray source and detector, to image at least a portion of a patient during at least a portion of the performance of at least one of a vertebroplasty procedure, a kyphoplasty procedure, an electroencephalography (EEG) procedure and intraoperative electromyography (EMG). The imaging system is arranged on a robot including at least four axes of rotation, and preferably at least 6 axes of rotation. In at least one further embodiment of the present application, an x-ray system is disclosed. The x-ray system includes an imaging system including an x-ray source and an x-ray detector; a table; and at least one robot. The table is movable by the at least one robot and the at least one other robot includes at least six axes of rotation and controls movement of the imaging system. Further, in at least one other embodiment, an x-ray system includes an imaging system including an x-ray source and an x-ray detector, a table, and at least two robots. The x-ray source and an x-ray detector are movable by the at least one robot and the at least one other robot, each including at least four axes of rotation, and preferably at least 6 axes of rotation to control movement.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIGS. 1A and 1B show examples of a robot 15 for use in at least one embodiment of the present application. These robots 15 are disclosed in U.S. application Ser. No. 11/373,698 filed Mar. 10, 2006 and entitled "X-Ray Device" and in German Application Number 10 2005 012 700.2 filed Mar. 18, 2005, the entire contents of each of which are hereby incorporated herein by reference. The robot 15 shown in FIG. 1A includes six axes of rotation as designated by elements A1-A6 in FIG. 1A.

More specifically, as shown in FIG. 1A, a turntable 2 is mounted to a base frame 1, which may be installed permanently on a floor, a wall, the ceiling, etc. of an examination/surgical room for example, so as to be capable of rotating about a first axes of rotation A1. A floating link 3 may be attached to the turntable 2 so as to be capable of swiveling about a second axis of rotation A2. An arm 4 may be fixed to the floating link 3 so as to be capable of rotating about a third axis of rotation A3. A hand 5 may be attached to the end of the arm 4 so as to be capable of rotating about a fourth axis of rotation A4. The hand 5 displays fixing element 6 which is capable of rotating about a rotational axis A6 and swiveling about a fifth axis of rotation A5 running perpendicular thereto.

FIG. 1B of the present application illustrates an example embodiment of the use of the robot 15 of FIG. 1A used in conjunction with a common support or holder 7. The holder may be connected, for example, to a fixing element 6 of the hand 5 of the robot 15. Any known type of connection, not shown, can be provided which allows for connection and disconnection of the holder 7.

The holder 7 can be designed in the manner of a U-section or U-arm (noting that the holder 7 can also be a C arm, for example) with two limbs opposed to each other 8a and 8b. An X-ray detector 9 can be attached to a first limb 8a and an X-ray source 10 can be attached to a second limb 8b, in an opposed arrangement. The first limb 8a and the second limb 8b can be attached so as to be capable of linear movement with reference to a central element 11 of the holder 7, so that a distance A between the X-ray detector 9 and the X-ray source 10 is adjustable for example.

Further, the imaging system including the X-ray source 10 and the X-ray detector 9 are arranged to be movable by a robot 15 including at least 6 axes of rotation. The X-ray source 10 and X-ray detector 9 can thus be part of an imaging system which can be used to image a patient (this can be used to perform any number of different types of imaging including but not limited to computed tomography (CT)-like images, other cross-sectional imaging, fluoroscopy, and angiographic imaging). It should be noted that for achieving cross sectional images, the C-arm system has to rotate at least 180 degrees around the patient.

The base frame 1 may be permanently installed on the floor, a wall, the ceiling, etc. of an examination/surgical room for example. With the aid of the robot 15, the holder or common support 7 can be traversed with reference to a patient accommodated on an examination table and brought into a predefined starting position (noting that in other embodiments of the present application to be explained hereafter, with regard to FIGS. 2-7, the table can be movable by a different robot or other device for example, or any other non-driven mechanics). Thereafter, the distance A can be set to a predefined value by adjusting the two limbs 8a and 8b. For this purpose, the limbs 8a and 8b can be moved in a linear manner by way of electric motor actuators for example. Further, it should be noted that the X-ray source 10 on limb 8b and the X-ray detector 9 on limb 8a can be used in a known manner to produce different types of imaging including but not limited to CT imaging, fluoroscopy (wherein lower doses of X-ray radiation are used), and angiographic imaging. Thus any imaging utilizing an X-ray source 10 and an X-ray detector 9 can be performed utilizing the robots 15 shown in FIGS. 1A and 1B of the present application.

Utilizing X-ray source 10 and X-ray detector 9, an extra exposure can be produced. It is also possible to rotate the holder or support 7 about a predefined axis for this purpose. This can involve the rotational axis A6, for example. It is further possible to rotate the holder 7 about the rotational axis A6 and traverse it axially with reference to the rotational axis A6 at the same time, for example. This will result in a spiral movement which will allow reconstruction of three-dimensional pictures of structures within the body and may be utilized with different types of cross-sectional imaging such as CT imaging for example.

It is also possible to control the rotary movement of the holder or support 7 about the rotational axis A6 by way of signals generated by bodily functions measured on the patient. Thus, the movement of the holder 7 can be controlled as a function of the heartbeat of the patient to be examined, for example. It is therefore possible to observe movements of the heart, and especially in a three-dimensional manner. Control of the robot 15 and control of the support or holder 7 can be affected under computer program control utilizing conventional techniques in a known manner (for example, in conjunction with interface 22 at the robot and proximate to the patient.

FIG. 2A of the present application shows a robot 15a, such as the robot with 6 degrees of freedom of FIGS. 1A and 1B for example, in first alternative configuration. In the configuration shown in FIGS. 2A-D, the robot 15a is shown as having the base plate 1 being mounted to a ceiling, such as the ceiling of an examination room, for example. In such a configuration, the robot 15 can be mounted to a ceiling and can be used to move a holder 7 (such as a C-arm or U-arm for example) including X-ray source 10 (along with an optional collimator 10a for example) and X-ray detector 9. An interface 22 at the robot (proximate to the patient) can be used to control the robot 15a, the patient positioning device (table 20 on which a patient is resting), and the X-ray source 10. There is no mechanical connection between the C-arm or U-arm holder 7 and the table 20. The table 20 may instead be movable by a floor mounted motorized (electric, hydraulic, etc.) device 24 which can change the height of the table 20, tilt (rotate) the table 20 and/or shift the table 20 backward or forward. The tilting/rotating is preferably done from a range of −15° to +120°.

It should be understood that movement of the table 20 is likely less requiring of a robot of at least six or even four axes of rotation, and thus the floor mounted motorized (electric, hydraulic, etc.) device 24 may be different from the robot 15 of FIGS. 1A and 1B and can have any type of conventional design. As illustrated in the example embodiment of FIG. 2A, the examination table 20 (on which a patient lies during examination/surgical procedures) can be movable at an angled position by the floor mounted motorized (electric, hydraulic, etc.) device 24 for subsequent imaging of the patient. In the example embodiment illustrated in FIG. 2A, the angled position ranges from −15° to +120°.

As shown in the example embodiment of FIG. 2B, the patient is positioned on the table 20 in a horizontal position. As shown in FIG. 2C, the table 20 (and thus the patient) can be movable at a tilted position of approximately 30° by the floor mounted motorized device 24. As shown in the example embodiment of FIG. 2D, the table 20 (and thus the patient) can be movable at a tilted position of approximately 60° by the floor mounted motorized device 24. In each of FIGS. 2B-2D above, only the table 20 and floor mounted motorized device 24 are shown, wherein the robot 15a and holder 7 (with other components as shown in FIG. 2A) being left out for the sake of brevity.

Figure 3:
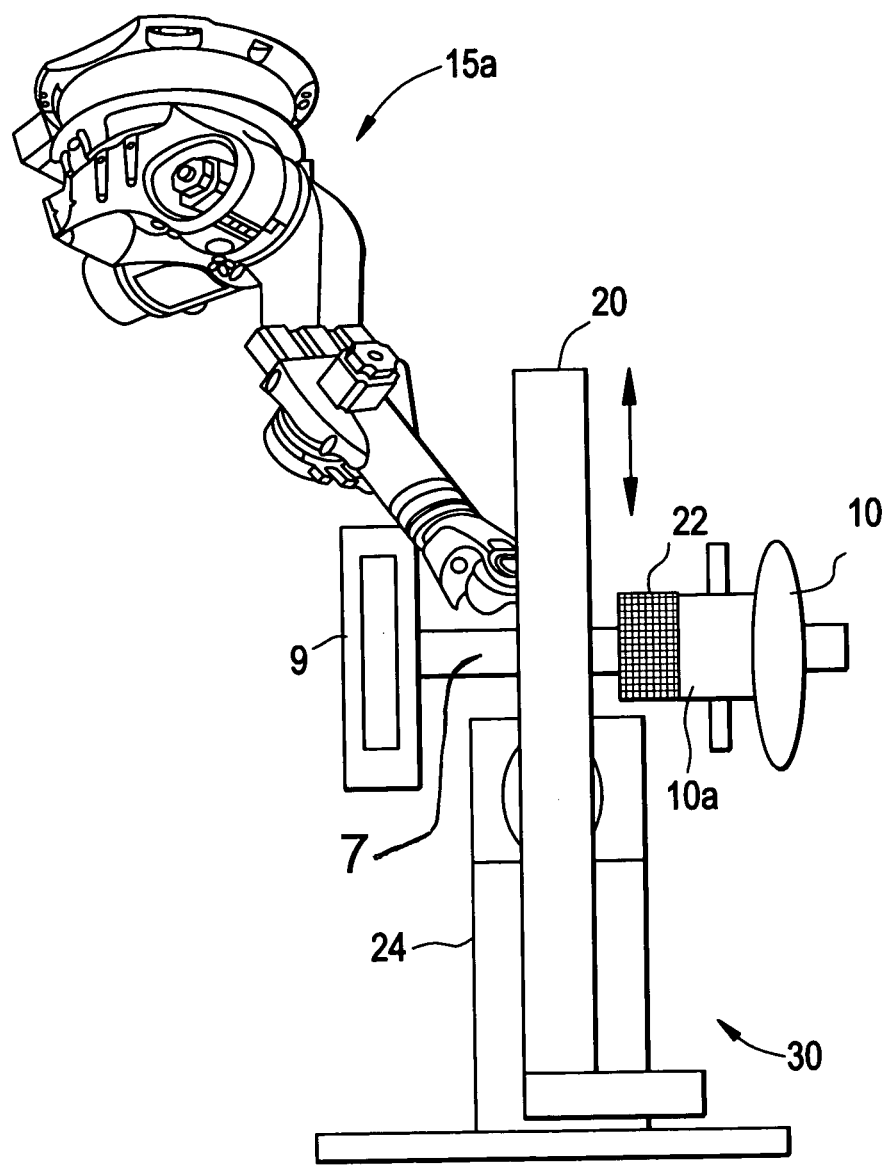
FIG. 3 illustrates an example embodiment of a ceiling mounted robotic system in combination with a tiltable table at a 90° angle.

Finally, as shown in the example embodiment of FIG. 3, the ceiling mounted robot 15a (of at least four degrees of freedom, preferably at least six degrees of freedom) can be usable to move the holder 7 relative to the table 20, wherein the table 20 is movable via floor mounted motorized device 24 so as to tilt the table in a substantially vertical position, namely at an angled position of substantially 90° (wherein the patient would have his feet approximately located at position 30). Such a table being tilted at an angle substantially 90° is especially useful to place a patient in an upright position to simulate different pressures on the spine. This can be especially important in vertebroplasty and kyphoplasty procedures to aid in determining how the techniques will adjust to different pressures on the spine.

Figure 4A:
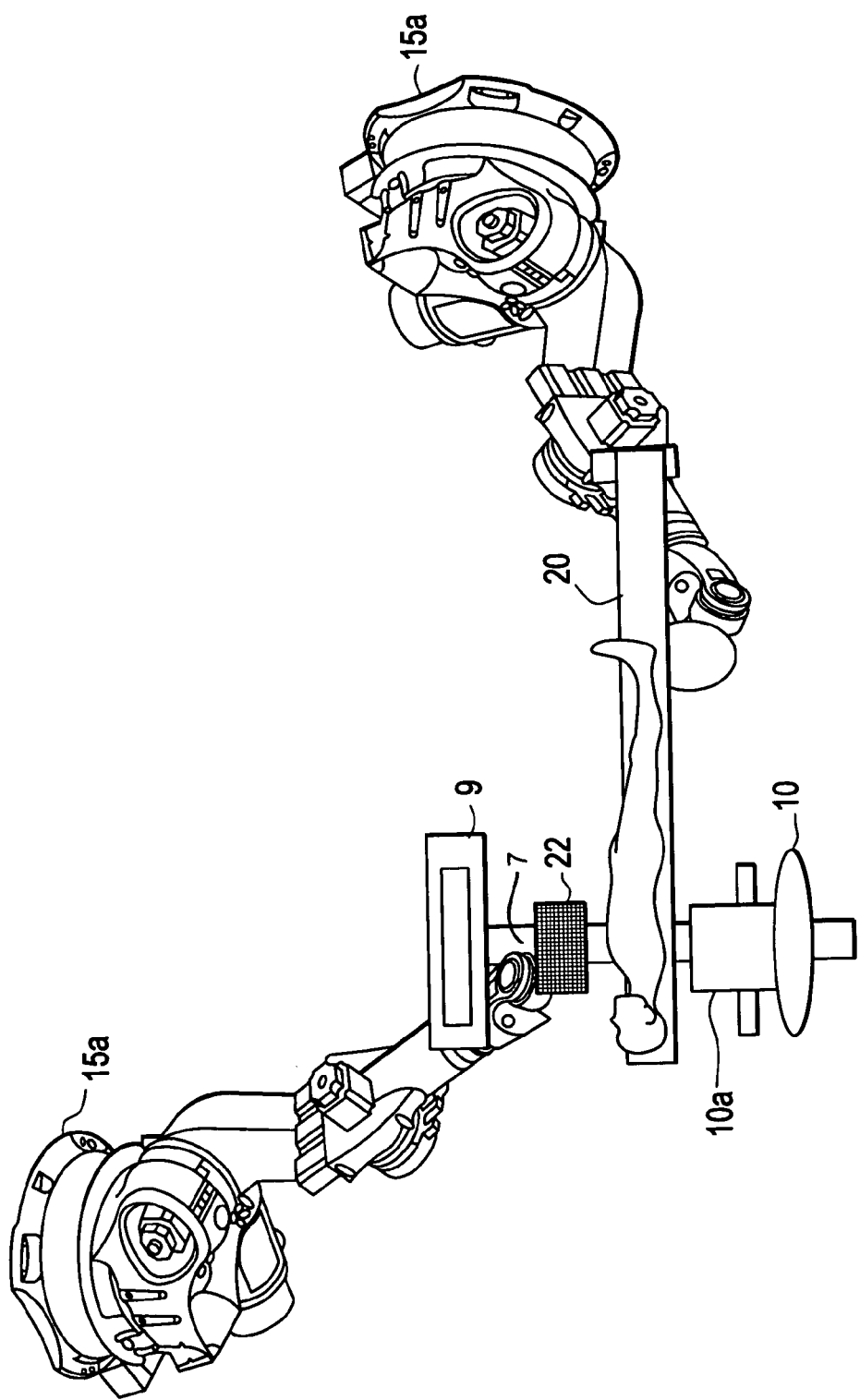

FIG. 4A illustrates an example embodiment of an X-ray system including a robot 15/15a of FIGS. 1-3 used to control the holder 7 (C-arm, U-arm, etc.) and a second robot used to control the table 20. The X-ray system includes an imaging system including a holder 7 with an X-ray source 10 and an X-ray detector 9, a table 20; and a plurality of robots. The table 20 is movable by one robot, and the imaging system including a holder 7 with an X-ray source 10 and an X-ray detector 9 is movable by at least one other robot 15/15a, noting that the at least one other robot 15/15a includes at least four axes of rotation (preferably six axes of rotation) to control movement of the imaging system (and noting that the robot used to control the table 20 may or may not be a robot including at least six or even at least four axes of rotation).

FIG. 4B illustrates an example embodiment of an X-ray system including a robot 15/15a of FIGS. 1-3 used to control an X-ray source 10 of the X-ray system and another robot 15/15a of FIGS. 1-3 used to control an X-ray detector 9 of the X-ray system. The table 20 is movable by a floor mounted motorized device 24. Thus, an X-ray source 10 and an X-ray detector 9 may be movable by separate robots 15/15a, noting that the robots 15/15a may include at least four axes of rotation (preferably six axes of rotation) to control movement of X-ray source 10 and an X-ray detector 9 of the imaging system.

Figure 4C:
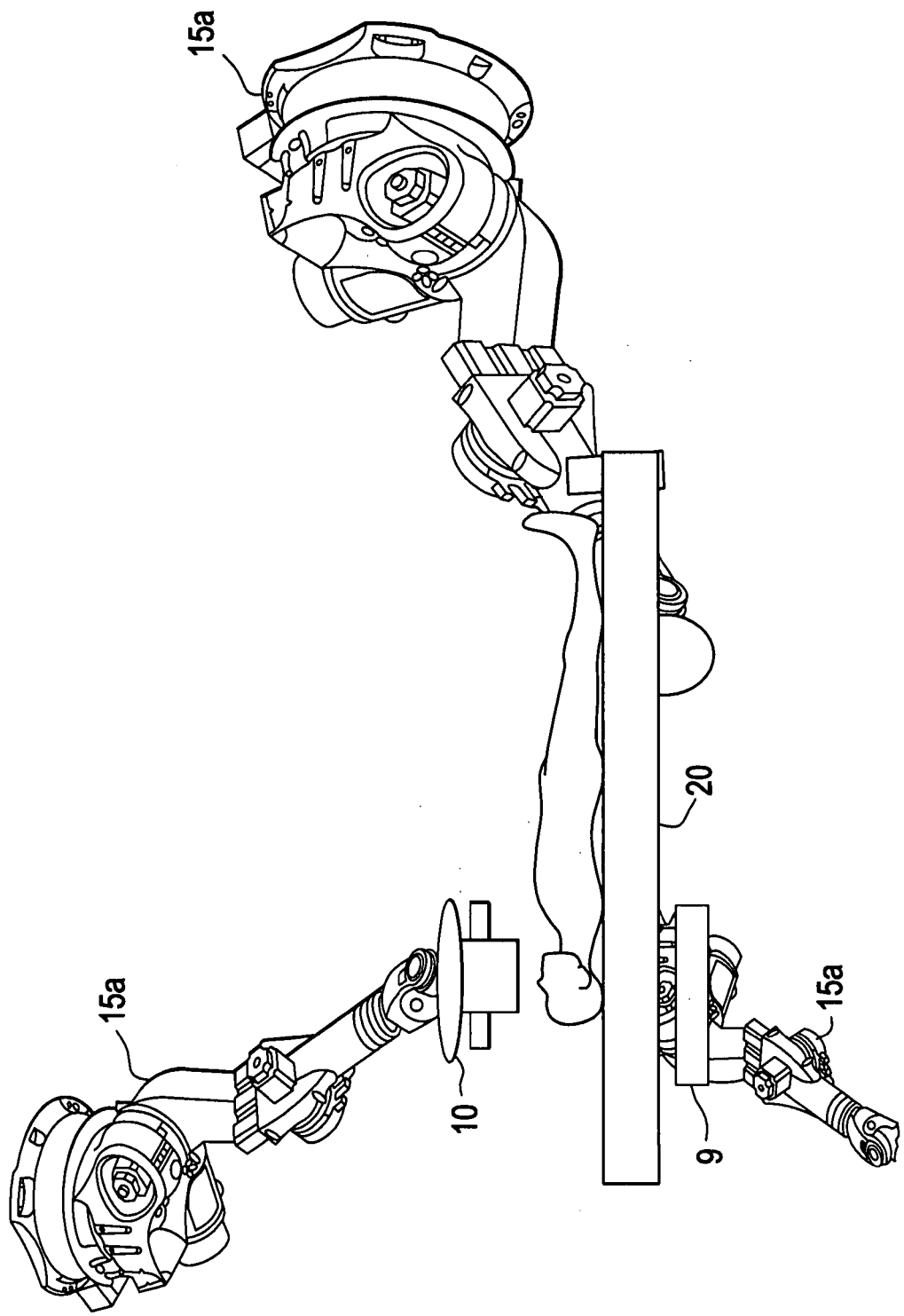

FIG. 4C illustrates an example embodiment of an X-ray system including a robot 15/15a of FIGS. 1-3 used to control an X-ray source 10 of the X-ray system and another robot 15/15a of FIGS. 1-3 used to control an X-ray detector 9 of the X-ray system. The table 20 is movable by a third robot 15/15a, such as one including at least four axes of rotation (preferably six axes of rotation). Thus, an X-ray source 10, an X-ray detector 9 and the table 20 may be movable by separate robots 15/15a, noting that the robots 15/15a may include at least four axes of rotation (preferably six axes of rotation) to control movement of X-ray source 10 and an X-ray detector 9 of the imaging system (and noting that the robot used to control the table 20 may be a floor mounted motorized device 24 or may be a robot 15/15a, such as one including at least four axes of rotation (preferably six axes of rotation)).

Example embodiments of methods of using any of the aforementioned robotic systems prior, during and subsequent to procedures of vertebroplasty and kyphoplasty will now be explained hereafter.

Figure 5:
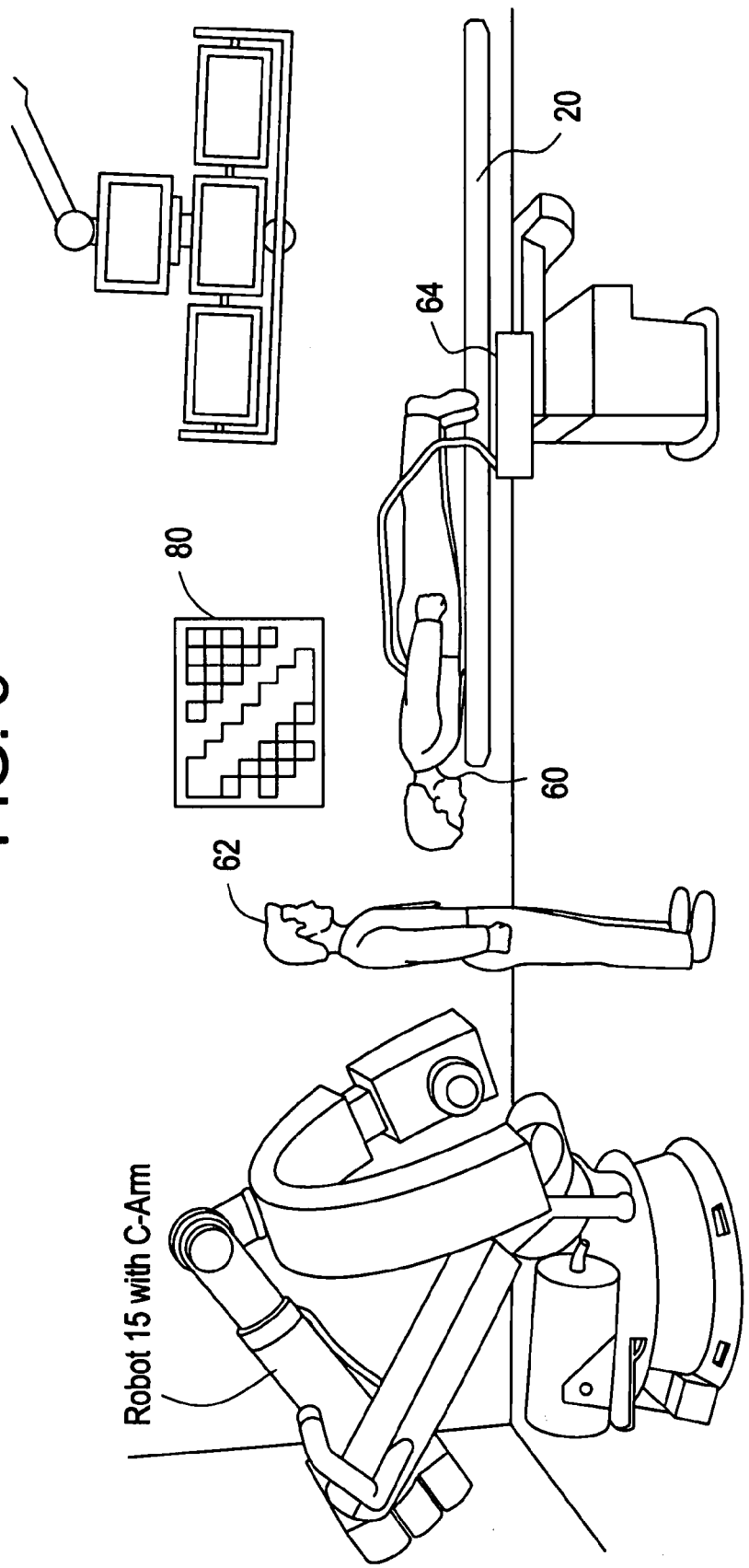
FIG. 5 illustrates an example embodiment of example robotic systems for use in conjunction with a vertebroplasty and/or kyphoplasty procedure.

As shown in FIG. 5, a method of an embodiment of the present application is directed to performing at least one of a vertebroplasty and a kyphoplasty procedure on a patient 60 and using an imaging system, including at least an X-ray source 10 and detector 9, to image at least a portion of the patient 60 during at least a portion of performance of the at least one of the vertebroplasty and the kyphoplasty procedure, wherein the imaging system is arranged on a robot 15 including at least four axes of rotation (preferably six axes of rotation). Such a robot 15 may be any of those shown in FIGS. 1A, 1B, 4 and 5 for example. The imaging system may include an X-ray source 10 and a detector 9 arranged on a common support 7, wherein the common support 7 is arranged on the robot 15 and is movable around the at least four axes of rotation (preferably six axes of rotation). In at least one embodiment of the present application, the imaging system may be used to perform combined fluoroscopic and cross-sectional imaging, at least one of computed tomography (CT)-like imaging and fluoroscopy, and/or at least one of fluoroscopic and angiographic imaging.

For example, by utilizing any of combined fluoroscopic and cross-sectional imaging, at least one of computed tomography (CT)-like imaging and fluoroscopy, and/or at least one of fluoroscopic and angiographic imaging techniques, in combination with a robot 15 as shown in FIGS. 1A and 1B of the present application, better access to a patient 60 can be gained by a doctor 62 during vertebroplasty and kyphoplasty procedures. As such, the doctor 62 can stand closer to the patient 60 and can perform the delicate vertebroplasty and/or kyphoplasty operation while receiving feedback, via display 80, via 2D/3D fluoroscopic, angiographic, CT, and/or other cross-sectional imaging information from the use of the aforementioned imaging system and the robot 15. For example, use of the robot 15 may permit the doctor 62 to stand closer to the patient 60 as the at least four (preferably at least six) axes of movement of the robot 15 provide greater freedom of movement. Other advantages of the robotic system in conjunction with such procedures may include easier positioning of the needles, etc. and/or the possibility of tilting the patient and thus getting information such as, for example, mechanical forces in an upright position of a patient.

Further, imaging such as fluoroscopy can be utilized, which decreases x-ray dosage which might otherwise harm the doctor 62. Utilizing fluoroscopy for example, an X-ray dose from the X-ray source 10 is substantially reduced from that of other imaging techniques (which is a benefit both to the patient 60 and to the doctor 62 performing the vertebroplasty and/or kyphoplasty procedures). Although the quality of the imaging will also be reduced, such imaging will still be good enough to allow the doctor 62 to guide the instrument during the vertebroplasty and/or kyphoplasty procedures. This, combined with the robot 15 including at least four (preferably at least six) axes of rotation, provides a system permitting good feedback to the doctor 62, while allowing the doctor 62 to remain close to the patient during the procedure.

As such, a new and unique method can be developed including imaging, using an imaging system including at least an X-ray source 10 and detector 9, at least a portion of a patient during at least a portion of at least one of vertebroplasty and kyphoplasty procedures, wherein the imaging system is arranged on a robot 15/15a including at least four (preferably at least six) axes of rotation, to substantially aid and improve the vertebroplasty and/or kyphoplasty procedure. Thus, the aforementioned imaging and robotic system can be used during at least a portion of the vertebroplasty and/or kyphoplasty procedures (such as, for example, during needle and/or balloon insertion or removal, insertion of the cement, etc.) and can attain new advantages and avoid problems such as those outlined hereafter.

For example, with fluoroscopy alone, paravetebral soft-tissue is not visible and for example paravertebral veins cannot be identified (which is important to know as cement might be falsely get into the veins, perhaps leading to pulmonary embolism). The complication of pulmonary cement drainage due to vertebroplasty has been reported. With two female patients with distinct osteoporosis and different genesis, the possible danger of cement drainage over the paravertebral veins to the pulmonary vasculature is demonstrated. Here a part of the arteries become embolized and cemented. Though these complications showed only low hemodynamic consequences, they are potentially dangerous and should be avoided by choosing the right indications. A distinct osteoporosis or infiltration with tumor cells seem to be predisposed to unintentional cement drainage. J Miner Stoffwechs 2004; 11 (Suppl 3): 15-18.) Such a system as the aforementioned imaging system and the robot 15 described with regard to FIGS. 1A, 1B, 4 and 5 above can utilize 2D/3D fluoroscopic, angiographic, CT, and/or other cross-sectional imaging information to combat such problems.

As shown in the example embodiment of FIG. 5 of the present application, for vertebroplasty and/or kyphoplasty procedures, the patient 60 may be initially transferred to a multipurpose room. The robotic system 15a may aid in transferring the patient 60 from a bed to a multifunctional table 20 (noting that the robotic system may include separate or a common robot for control of each of the table 20 and imaging system including at least an X-ray source 10 and detector 9). This table 20 can further be controlled by another robot 15a or device 24, in a manner previously described with regard to FIGS. 2A-4C of the present application (noting that the system may include separate device 24 or a robot 15/15a for control of each of the table 20 and imaging system and or imaging system components including at least an X-ray source 10 and detector 9). During a treatment/procedure utilizing a vertebroplasty device (or kyphoplasty device) 64, the patient 60 is normally positioned face down as shown in FIG. 5.

Thereafter, the doctor 62 can move relatively closer to the patient 60, and can begin the procedure. During the procedure, the robot 15 (as shown in FIG. 5 with a C-arm, for example, including an imaging system including at least an X-ray source 10 and detector 9) can be used to image the patient 60 to provide imaging information, such as cross-sectional images via CT-like imaging for example (to provide, for example, information on soft tissue and trabecular structure of the bone) via rotational imaging 3D reconstruction. By use of a robotic system with at least four (preferably at least six) axes of rotation, imaging, such as cross-sectional imaging via CT-like imaging for example, is possible even with the doctor 62 standing very close to the patient 60, as shown in FIG. 5 for example. This allows for a more accurate procedure. In addition, other advantages of this combined workflow using a robotic system including robot 15/15a can include better patient access, better handling of the devices as more degrees of freedom are available to position the holder 7 (C-arm, U-arm, etc.), the possibility to treat a patient in an upright position thus simulating mechanical force, the combination of real-time fluoroscopy and cross-sectional imaging, etc.

Further, in the past, vertebroplasty and/or kyphoplasty were only done with the patient in a horizontal position (namely on his stomach as shown in FIG. 5). However, this may not provide a great deal of functional information. The inventors of the present application discovered that if the patient 60 were placed in a more upright position, for example at an angled position of substantially 90°, pressures would be placed on the spine. Accordingly, the inventors of the present application discovered that they can utilize the robot 15a or a device 24 for controlling the table 20, in a manner shown in FIGS. 2A-2D and FIG. 3 for example, to adjust the patient at different angles (ranging from −15° to +120°s, for example), and including an angle of substantially 90° (FIG. 3 for example), to provide morphological as well as functional imaging (e.g. by placing the patient in an upright, head-tilted, or sitting position, mechanical forces on the affected and/or treated vertebral bodies and the whole spine can be simulated).

As such, further imaging (including, but not limited to, any of 2D/3D fluoroscopic, angiographic, CT-like, and/or other cross-sectional imaging) can take place utilizing the imaging system shown in FIG. 5, with the patient 60 in an upright position (illustrated by FIG. 3 for example). Alternatively, the patient can be placed in a head-tilted or sitting position, or at any other angled position, to simulate different pressure conditions on the spine, and thereafter imaging, via the aforementioned techniques and utilizing robot 15 of at least four (preferably at least six) axes of rotation and including at least an X-ray source 10 and detector 9, can take place. As such, fast diagnostic imaging can take place, as well as imaging which provides instant feedback in a manner which permits the doctor 62 to be readily accessible to the patient, a situation which is ideal for vertebroplasty and kyphoplasty procedures.

Thus, in such a methodology, the table 20 is movable, via at least one of a robot 15/15a and a device 24 to place the patient in an angled position (for example, in a substantially vertical position) before performing at least one of the vertebroplasty and kyphoplasty procedures on the patient 60. Further, the imaging system is movable via at least one robot 15/15a including at least 6 axes of rotation to image at least a portion of the patient in the angled position (for example in a substantially upright position) during the performance of at least one of a vertebroplasty and kyphoplasty procedure. Further, instead of the imaging system being movable via the robot 15/15a, the common support or holder 7 may be movable via the robot 15/15a (and/or the components thereof may be separately movable as shown in FIG. 4B for example). Still further, such a common support 7 may, but need not, include a C-arm or U-arm for example. Again, the imaging to be performed may include any type of imaging including, for example, any combination of CT-like imaging, fluoroscopy, angiographic imaging, and any other cross-sectional imaging.

In addition, other procedures are possible utilizing such a system of robot(s) controlling one or both of an imaging system, including an X-ray source and an X-ray detector 9, and a table 20. These procedures can include osteoporosis measurement or analysis to obtain quantitative information about such things as bone marrow density of the affected vertebrae, as well as adjacent vertebrae for example. For this, additional measurements using a calibration phantom may also be utilized. In addition, intravenous or intra-arterial contrast injections can be performed to more easily, when imaged, visualize arterial and or venous vessels adjacent to the vertebral bodies to be treated. Accordingly, by such a system, vertebroplasty and/or kyphoplasty with fluoroscopic and/or cross-sectional guidance may be performed.

Again, the patient can be treated in an upright, head-tilted, or sitting position and a real time 2D/3D or 3D/3D image overlay based puncture guidance can be performed. In addition, magnetic tracking may be used in order to place the needle in the designated areas of the spine, semi-automatically, in combination with any of the aforementioned imaging techniques and robotic systems. Further, post-procedural control can be provided, utilizing at least one of fluoroscopic and/or cross-sectional, angiographic, and/or CT-like imaging via the robotic systems described above. Further, the imaging system, arranged under movement control of the robot including at least four (preferably at least six) axes of rotation, may be used to image at least a portion of the patient near the end and/or subsequent to the performance of at least a portion of the at least one of the vertebroplasty and kyphoplasty procedure, so as to control post-procedural removal of the needle in a manner similar to that of insertion of the needle and cement, for example. In addition, the patient may be repositioned in any number of ways, and imaged utilizing any number of different types of imaging techniques, via the aforementioned device 24 and/or robotic controls of the imaging system, and/or the table 20.

Figure 6:
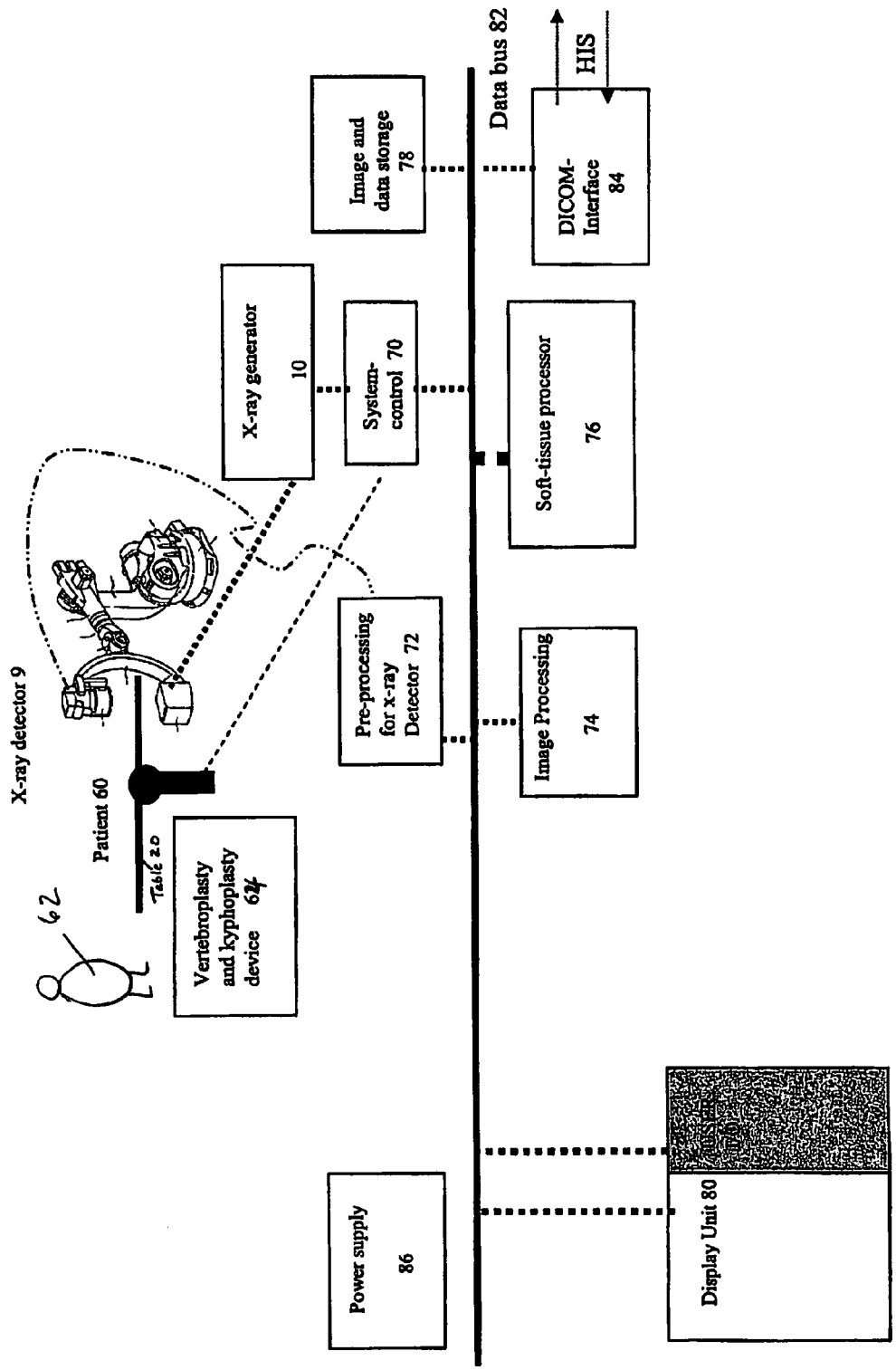
FIG. 6 illustrates an example embodiment of a system overview of example robotic systems for use in conjunction with a vertebroplasty or kyphoplasty procedure.

FIG. 6 provides an example embodiment of an overall system overview, usable with the embodiments previously described. As shown in FIG. 6, a patient 60 is laying on a table 20. The table 20 may be controllable by a first robot 15/15a or device 24, wherein a second robot 15/15a may include at least six axes of rotation and may be usable to control an X-ray detector 9, and X-ray generator 10. The actual generation of the X-rays via the X-ray generator 10 can be achieved via system control 70, which can be used to further control operation of any of the robots 15, 15a. FIG. 6 further illustrates pre-processing control 72 for control of the X-ray detector 9, as well as image processing device 74 and soft tissue processor 76 for processing the images obtained by the X-ray detector 9 in a known manner.

The obtained imaging information can be stored in an image and data storage device 78 and can further be displayed in a known manner on a display unit 80 for viewing by the doctor 62 for example. Thus, the doctor 62 can be provided with real time information to aid the doctor 62 in guiding the instrument and inserting the cement during the vertebroplasty and/or kyphoplasty procedures, during removal of the needle thereof, etc. Finally, a data bus 82 and interface 84 are additionally shown for transmitting the information to additional locations (such as a hospital information system (HIS), radiology information system (RIS), picture archiving and communication system (PACS), etc.), as well as a power supply 86 for supplying power to at least one or more of the X-ray detector 9, X-ray generator 10, robots 15, 15a, etc.

In addition, the above-described robotic controlled imaging system (and device or robotic controlled table) of FIGS. 1-6 can also be used for other procedures in addition to vertebroplasty and/or kyphoplasty procedures. For example, they may be applied to electroencephalography (EEG) procedures.

As a neurological diagnostic test, EEG has more than 60 years history and has evolved from analog EEG recording to the current digital recording, having advanced computerized data analysis system. EEG is recorded from the multiple electrodes placed over the scalp. The most common diagnostic utility of EEG is to establish diagnosis of seizure or seizure type, or spells (paroxysmal disorder) of unknown etiology. EEG tests may be performed for many other neurological disorders such as brain tumors, strokes, encephalitis, encephalopathy, degenerative or demyelinating diseases, etc.

EEG is recorded from multiple electrodes placed from the scalp. The recording is done while the patient is on the bed or in the reclining chair. The patient is asked to relax with eyes closed and encouraged to sleep during the recording. The EEG technologist performs the test and keeps eyes on the recording that appears on the video screen throughout the testing time. The preparation time for EEG record is 30 minutes and recording time is about 30 to 60 minutes. The patient may be sedated if indicated or needed to obtain sleep record.

In the field of EEG, various tests may benefit from a use of the above-described robotic controlled imaging system (and device or robotic controlled table) of FIGS. 1-6 with at least four (preferably at least six) axes of rotation. For example, the evoked potential (EP) test is one which may benefit. In the EP test, an electrical response is recorded from the brain, spinal cord or peripheral nerve evoked by various external stimuli, such as visual, auditory or somatosensory stimulation. The recording electrodes are placed over the scalp, neck or spine surface, which vary depending on the type of stimulus modality to be tested. As such, use of the above-described robotic controlled imaging system (and device or robotic controlled table) of FIGS. 1-6, with at least four (preferably at least six) axes of rotation, would permit a doctor to remain close to the patient during the procedure while the images are being recorded.

The Visual Evoked Potential (VEP) test examines the integrity of visual pathway from retina to occipital cortex where visual input is perceived in the brain. During the test, the patient is asked to watch the video screen, which present moving checkerboard patterns. If the patient wears glasses, VEP should be tested with the best corrected glasses. Each eye is tested separately. The preparation for VEP takes about 20 minutes and recording time of 30 minutes. VEP may be tested for patient with suspected diagnosis of multiple sclerosis, with complaint of visual disturbance, or with suspected lesion involving visual pathway. Again, use of the above-described robotic controlled imaging system (and device or robotic controlled table) of FIGS. 1-6 with at least four (preferably at least six) axes of rotation would permit a doctor to remain close to the patient during the procedure while the images are being recorded.

The Brainstem Auditory Evoked Potential (BAEP) test examines the integrity of auditory pathway through the brainstem. The sound enters ear canal and stimulates auditory nerve. The electrical impulse travels from auditory nerve through the brainstem to auditory cortex. During testing, the patient hears the repetitive click sound through the earphone. Each ear is tested separately. The preparation time for BAEP is 20 and recording time is about 30 minutes. BAEP may be tested for patients with hearing problem, dizziness or any lesion involving brainstem. BAEP may also be examined in patients with suspected diagnosis of multiple sclerosis. Again, use of the above-described robotic controlled imaging system (and device or robotic controlled table) of FIGS. 1-6 would permit a doctor to remain close to the patient during the procedure while the images are being recorded.

The Somatosensory Evoked Potential (SEP) test examines the sensory system from the peripheral nerve to the sensory cortex of brain. The weak electrical stimulations are applied to the peripheral nerve, for example median or ulnar nerve for upper extremity study and tibial nerve for lower extremity study. The patient feels tingling sensation with the electrical stimulation applied to the nerve but usually not painful. The preparation time for SEP is 30 minutes and recording time is 30 to 60 minutes. In some patients, both upper and lower extremity SEPs are tested. SEP may be tested in patients with numbness or weakness of arm or leg, or with suspected lesion in spinal cord or peripheral nerve. SEP is also common diagnostic test for multiple sclerosis. Again, use of the above-described robotic controlled imaging system (and device or robotic controlled table) of FIGS. 1-6 with at least four (preferably at least six) axes of rotation would permit a doctor to remain close to the patient during the procedure while the images are being recorded.

Further, Neurophysiological Monitoring during Surgery (Intra-operative Monitoring or—IOM) may also benefit from the above-described robotic controlled imaging system (and device or robotic controlled table) of FIGS. 1-6 with at least four (preferably at least six) axes of rotation, as it again would permit a doctor to remain close to the patient during the procedure while the images are being recorded.

For example, a patient who undergoes brain, spinal cord or spine surgery may have potential risk for damaging the nervous system. In order to avoid neurological damage to peripheral nerve, spinal cord, brainstem or brain during surgery, various neurophysiological testing have been developed. In the laboratory, operating rooms typically have an Internet connection for transmitting EEG or EP data from operating room to review station in the EEG laboratories. As such, use of the above-described robotic controlled imaging system (and device or robotic controlled table) of FIGS. 1-6 with at least four (preferably at least six) axes of rotation would thus provide a huge benefit.

EEG monitoring is done most commonly during surgery of carotid artery, for example, carotid endarterectomy. EEG is a sensitive tool to reflect brain ischemia during cross clamping of the carotid artery. If EEG changes after cross clamping of the artery, shunt placement is required to restore the blood circulation to the brain and to avoid ischemic damage to the brain. Thus, use of the above-described robotic controlled imaging system (and device or robotic controlled table) of FIGS. 1-6 with at least four (preferably at least six) axes of rotation would permit a doctor to remain close to the patient during the procedure while the images are being recorded.

Brainstem Auditory Evoked Potential Monitoring (BAEP) monitoring is requested by surgeons for surgery of brainstem, for example, removal of acoustic tumor, vascular decompression of trigeminal nerve for trigeminal neuralgia or vascular decompression of facial nerves for facial spasms. Auditory nerve or brainstem is at risk during these surgeries. Monitoring BAEP helps to identify potential risk and to prevent permanent damage to auditory nerve or brainstem. Again, use of the above-described robotic controlled imaging system (and device or robotic controlled table) of FIGS. 1-6 with at least four (preferably at least six) axes of rotation would permit a doctor to remain close to the patient during the procedure while the images are being recorded.

Somatosensory Evoked Potential Monitoring (SEP Monitoring) monitoring is used for testing spinal cord function for surgeries of spine or spinal cord such as scoliosis, laminectomy, spine fusion or spinal cord tumor surgeries, etc. For cervical spine or cervical cord surgery, upper extremity SEP is usually tested by stimulation median or ulnar nerve. For thoracis/lumbar spine or cord surgery, posterior tibial nerve is stimulated. Changes of SEP during surgery will provide warning signs to surgeons before permanent spinal cord damage occurs. Again, use of the above-described robotic controlled imaging system (and device or robotic controlled table) of FIGS. 1-6 with at least four (preferably at least six) axes of rotation would permit a doctor to remain close to the patient during the procedure while the images are being recorded.

Motor Evoked Potential Monitoring (MEP monitoring) is similar to SEP monitoring. Although SEP monitoring is usually sufficient to protect spinal cord damage, there have been cases in which SEP remained unchanged during surgery, but the patient ended up with motor deficit. This is because SEP deals only with sensory system but not motor system. Ideal monitoring for spinal cord function is to combine both SEP and MEP monitoring. MEP is performed by electrically stimulating brain via electrodes placed over the scalp (same electrodes with EEG recording). High stimulus intensity current is painful if applied during awake but the patient will not perceive any pain during anesthesia. Responses are recorded from spinal cord or muscles. MEP monitoring may be avoided in patients who has history of epilepsy or potential seizure risk secondary to various brain diseases or patient who has implanted metallic device in the brain. Again, use of the above-described robotic controlled imaging system (and device or robotic controlled table) of FIGS. 1-6 with at least four (preferably at least six) axes of rotation would permit a doctor to remain close to the patient during the procedure while the images are being recorded.

In addition, use of the above-described robotic controlled imaging system (and device or robotic controlled table) of FIGS. 1-6 with at least four (preferably at least six) axes of rotation would be beneficial in conjunction with Intraoperative electromyography monitoring in minimally invasive transforaminal lumbar interbody fusion. Minimally invasive transforaminal lumbar interbody fusion (TLIF) is an increasingly popular method for achieving lumbar decompression and fusion. The procedure is technically more demanding than open fusion, with correspondingly more theoretical risk of complication.

The use of intraoperative electromyography (EMG) may be used as an adjunct to surgery to reduce the risk of complications. Thus, in addition, the above-described robotic controlled imaging system (and device or robotic controlled table) of FIGS. 1-6 with at least four (preferably at least six) axes of rotation can also be used for other procedures in addition to vertebroplasty and/or kyphoplasty procedures. For example, they may be applied to intraoperative electromyography (EMG).

A continuous stimulation pedicle access needle alerts the surgeon to incorrect medial trajectories and may lead to safer pedicle cannulation. Intraoperative nerve root monitoring is a useful adjunct to minimally invasive TLIF. Accordingly, use of the above-described robotic controlled imaging system (and device or robotic controlled table) of FIGS. 1-6 with at least four (preferably at least six) axes of rotation would permit a doctor to remain close to the patient during the procedure while the images are being recorded and may benefit intraoperative electromyography (EMG) procedures.

As shown in FIG. 7, the same system of FIG. 6 may be used, with the addition of any other device used for any of the above-mentioned procedures. For example, an EEG device 90 can be added, and/or and EMG device 92. The remaining components can be the same as previously described with regard to FIG. 6, and/or and of FIGS. 1-6 of the application.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method comprising:
   performing at least one of a vertebroplasty procedure and a kyphoplasty procedure on a patient;
   using an imaging system, including at least an x-ray source and a detector, to image at least a portion of the patient during the performance of at least a portion of the at least one of a vertebroplasty procedure and a kyphoplasty procedure, the imaging system being arranged on at least two imaging system robots including at least four axes of rotation, wherein the x-ray source is movable by one of the at least two imaging system robots and the detector is movable by an other of the at least two imaging system robots independently of the x-ray source, the using an imaging system including,
   moving the imaging system, via the at least two imaging system robots including at least four axes of rotation, to image at least a portion of the patient in a substantially upright position during an injection, the injection being at least a portion of the performing; and using a table to support the patient, the using a table including, moving the table to adjust the patient independent of the imaging system, and the table being attached to at least one table robot, the at least one table robot being a robot other than the at least two imaging system robots, and moving the table, via the at least one table robot, to place the patient in a substantially vertical position to simulate mechanical forces before performing the at least one of a vertebroplasty procedure and a kyphoplasty procedure on the patient.

2. The method of claim 1, wherein the table is moved, via the at least one table robot, to place the patient in an angled position before performing the at least one of a vertebroplasty procedure and a kyphoplasty procedure on the patient, and wherein the imaging system is moved, via the at least two imaging system robots including at least four axes of rotation, to image at least a portion of the patient in the angled position during at least a portion of the performance of the at least one of a vertebroplasty procedure and a kyphoplasty procedure.

3. The method of claim 2, wherein the imaging system is used to perform at least one of computed tomography (CT)-like imaging and fluoroscopy.

4. The method of claim 2, wherein the imaging system is used to perform at least one of fluoroscopic and angiographic imaging.

5. The method of claim 2, wherein the imaging system is used to perform combined fluoroscopic and cross-sectional imaging.

6. The method of claim 2, wherein the angled position includes an angle ranging from −15 degrees to 120 degrees.

7. The method of claim 1, wherein the imaging system, arranged on the at least two imaging system robots including at least four axes of rotation, is used to image at least a portion of the patient subsequent to the performance of the at least one of a vertebroplasty procedure and a kyphoplasty procedure.

8. The method of claim 7, wherein the at least two imaging system robots includes at least six axes of rotation.

9. The method of claim 1, wherein the imaging system is used to perform at least one of computed tomography (CT)-like imaging and fluoroscopy.

10. The method of claim 1, wherein the imaging system is used to perform at least one of fluoroscopic and angiographic imaging.

11. The method of claim 1, wherein the imaging system is used to perform combined fluoroscopic and cross-sectional imaging.

12. The method of claim 1, wherein the at least two imaging system robots includes at least six axes of rotation.

13. A method comprising:

performing at least one of a vertebroplasty procedure and a kyphoplasty procedure on a patient;

using an imaging system, including at least an x-ray source and a detector, to image at least a portion of the patient during the performance of at least a portion of the at least one of a vertebroplasty procedure and a kyphoplasty procedure, the imaging system arranged on a common support, the common support being arranged on an imaging system robot and being movable around the at least four axes of rotation;

moving the common support, via the imaging system robot including at least four axes of rotation, to image at least a portion of the patient in a substantially upright position during an injection, the injection being at least a portion of the performing; and using a table to support the patient, the using a table including, moving the table to adjust the patient independent of the imaging system, and the table being attached to at least one table robot, the at least one table robot being a robot other than the imaging system robot, moving the table, via the at least one table robot, to place the patient in a substantially vertical position to simulate mechanical forces before the performing.

14. The method of claim 13, wherein the common support includes a C-arm.

15. The method of claim 13, wherein the table is moved, via the at least one table robot, to place the patient in an angled position before performing the at least one of a vertebroplasty procedure and a kyphoplasty procedure on the patient, and wherein the imaging system is moved, via the imaging system robot including at least four axes of rotation, to image at least a portion of the patient in the angled position during at least a portion of the performance of the at least one of a vertebroplasty procedure and a kyphoplasty procedure.

16. The method of claim 15, wherein the imaging system is used to perform at least one of computed tomography (CT)-like imaging and fluoroscopy.

17. The method of claim 15, wherein the imaging system is used to perform at least one of fluoroscopic and angiographic imaging.

18. The method of claim 15, wherein the imaging system is used to perform combined fluoroscopic and cross-sectional imaging.

19. The method of claim 15, wherein the angled position includes an angle ranging from −15 degrees to 120 degrees.

20. The method of claim 13, wherein the imaging system is used to perform at least one of fluoroscopic and angiographic imaging.

21. The method of claim 13, wherein the imaging system is used to perform combined fluoroscopic and cross-sectional imaging.

22. The method of claim 13, wherein the imaging system robot includes at least six axes of rotation.

23. A method comprising:

imaging, using an imaging system including at least an x-ray source and detector, at least a portion of a patient during an injection, the injection being at least a portion of at least one of a vertebroplasty procedure and a kyphoplasty procedure, the imaging system being arranged on at least two imaging system robots including at least four axes of rotation, the imaging including, moving the x-ray source by one of the at least two imaging system robots and the detector by another of the at least two imaging system robots independently of the x-ray source; and using a table to support the patient, the table being attached to a device to move the table, the using a table including, moving the table, independent of the imaging system, via at least the device attached to the table, to place the patient in an angled position before performing the at least one of a vertebroplasty procedure and a kyphoplasty procedure on the patient, and the imaging further including, moving the imaging system, via the at least two imaging system robots including at least four axes of rotation, to image at least a portion of the patient in the angled position during at least a portion of the at least one of a vertebroplasty procedure and a kyphoplasty procedure.

24. The method of claim 23, wherein the angled position includes an angle of substantially 90 degrees.

25. The method of claim 23, wherein the imaging system is used to perform at least one of computed tomography (CT)-like imaging and fluoroscopy.

26. The method of claim 23, wherein the imaging system is used to perform combined fluoroscopic and cross-sectional imaging.

27. The method of claim 23, wherein the angled position includes an angle ranging from −15 degrees to 120 degrees.

28. The method of claim 23, wherein the at least two imaging system robots includes at least six axes of rotation.

* * * * *